United States Patent

Byatt et al.

[11] Patent Number: 6,161,426
[45] Date of Patent: Dec. 19, 2000

[54] PHOTOACOUSTIC FREE FALL MEASURING CELL

[75] Inventors: John Anthony Byatt, Klingnau; Thomas Kleiner, Rieden-Nussbaumen; Daniel Matter, Brugg, all of Switzerland; Günter Spanner, München, Germany

[73] Assignee: ABB Research Ltd., Zurich, Switzerland

[21] Appl. No.: 09/168,884

[22] Filed: Oct. 9, 1998

[30]     Foreign Application Priority Data

Oct. 9, 1997 [DE] Germany .............................. 197 44 500

[51] Int. Cl.⁷ .......................... G01N 29/00; G01N 21/01; G01B 9/02
[52] U.S. Cl. ...................... 73/61.49; 356/349; 250/432 R
[58] Field of Search ................................ 73/61.49, 61.58; 356/349, 357, 432; 250/432 R

[56]            References Cited

U.S. PATENT DOCUMENTS

| | | |
|---|---|---|
| 3,987,304 | 10/1976 | Kreuzer . |
| 4,080,837 | 3/1978 | Alexander et al. . |
| 4,413,504 | 11/1983 | Voigtman et al. ..................... 61/61.58 |
| 5,125,749 | 6/1992 | Leugers et al. . |
| 5,339,674 | 8/1994 | Hammerich et al. . |
| 5,489,977 | 2/1996 | Winslow et al. . |
| 5,718,226 | 2/1998 | Riza ........................................ 600/437 |
| 5,781,294 | 7/1998 | Nakata et al. ........................... 356/349 |
| 5,926,273 | 7/1999 | Kimura et al. ........................... 356/349 |

FOREIGN PATENT DOCUMENTS 2 089 041   6/1982   United Kingdom .

OTHER PUBLICATIONS

Edward P.C. Lai and Robert S. Vucic; "Kinetic Study of the Degradation of Lubricating Motor Oil by Liquid Chromatography and Photoacoustic Spectrometry"; Fresenius J Anal Chem (1993) 347; pp. 417–422.

P. Hodgson et al.; "Application of Pulsed Laser Photoacoustic Sensors in Monitoring Oil Contamination in Water"; Sensors and Actuators B29 (1995); pp. 339–344.

H.A. MacKenzie et al.; "A Laser Photoacoustic Sensor for Analyte Detection in Aqueous Systems"; Sensors and Actuators B, 11, pp. 213–220 (1993) (Discussed in Specification).

Jean–Pierre Monchalin; "Optical Detection for Ultrasound", IEEE Transactions on Ultrasonics, Ferroelectrics and Frequency Control 33 (5), pp. 485–499 (1986) (Discussed in the specification).

Detection of photoacoustic waves in liquids by fibre optic interferometry by D.P. Hand, et al, published in Optics Communications, pp. 1–6.

*Primary Examiner*—Hezron Williams
*Assistant Examiner*—Jay L. Politzer
*Attorney, Agent, or Firm*—Oblon, Spivak, McClelland, Maier & Neustadt, P.C.

[57]            ABSTRACT

A photoacoustic flow measuring cell (1a, 1b) for measuring oil residues in water including a photoacoustic sensor principle based on converting optical energy into acoustic energy by absorption of light on oil molecules in water. A measuring cell (1a, 1b) having contamination-free infeed optics (9, 10, 11, 21) is produced by providing a free fall stage (3) for a contactless feed (12) of light into an analyte (4). A sound detector (16) is an externally mounted piezoelectric transducer (16) or an optical interferometer (23) which measures vibrations of a liquid surface (6) without contacting the same. The photoacoustic free fall measuring cell (1a, 1b) provides a high level of detection, well into the ppm concentration range, low susceptibility to faults and is suitable, in particular, for use in high pressure separating tanks (28) for conveyance of crude oil.

7 Claims, 5 Drawing Sheets

PHOTOACOUSTIC FREE FALL MEASURING CELL

BACKGROUND OF THE INVENTION

1. Field of the Invention

The invention relates to the field of photoacoustic spectroscopy for the detection of impurities in liquid media. It proceeds from a photoacoustic flow measuring cell according to the preamble of claim 1.

2. Discussion of Background

In the offshore conveyance of crude oil, so-called separating tanks are used, in which the various phases (sand, water, oil and gas) occurring during drilling or conveyance are separated by virtue of their density differences and are discharged in separate line systems. In this case, even slight oil impurities in the waste water may lead to unacceptable environmental pollution, with the corresponding consequences as regards cost. Typical concentration limit values for oil in water are 40 ppm in the case of direct disposal into the ocean and 100 ppm–5000 ppm in the case of reuse as process water, for example when pumped back into the oil source. In order to monitor the limit values, therefore, it is necessary to have detection-sensitive and reliable oil residue detectors.

High pressure separating tanks have recently been developed, which are suitable for operating on the ocean floor a few hundred meters below the surface of the ocean. Conveyed and already separated oil can then be pumped to the surface of the ocean with a much lower expenditure of energy. Such separating tanks are exposed to very high pressures of 60–180 bar, specifically, from outside, to the water pressure at the bottom of the ocean and, from the inside, to the pressure of the conveyed crude oil, as well as to high temperatures of 50–120° C. An oil residue detector must be operational for a period of years, and without requiring maintenance, under these difficult operating conditions, since operating failure and premature replacement would incur high costs.

Photoacoustic sensors for trace analysis in liquids and, in particular, of oil in water are known from the article by H. A. MacKenzie et al., "A laser photoacoustic sensor for analyte detection in aqueous systems", Sensors and Actuators B, 11, 213-220 (1993). The photoacoustic measuring method is based on converting optical energy into acoustic energy by means of foreign molecules in liquids. Intensive pulsed laser radiation is transmitted to a measuring cell, is absorbed by the molecules to be detected and is converted into thermal energy by relaxation without radiation. Local heating in the absorption region leads to thermal expansion and to the radiation of an acoustic pressure wave. The frequency of the acoustic wave is determined by the repetition rate or modulation frequency of the laser radiation. The excitation efficiency is proportional to the laser pulse energy absorbed, to the coefficient of thermal expansion and to the sound velocity and is inversely proportional to the heat capacity. Advantageously, the wavelength is selected in such a way that absorption is low in the medium and high in the foreign molecules. The degree of detection of impurities is a plurality of orders of magnitude better in the case of high laser pulse energies and in short measuring cells than in the case of direct infrared, transmission or reflectance spectroscopy.

In measuring cells for aggressive or coating-forming analytes, the contamination of sensor components, such as, for example, the optical apertures or else the acoustic detectors, presents a considerable problem. U.S. Pat. No. 5,125,749 discloses a photoacoustic flow measuring cell for liquids, in which a sensor head is equipped with a fiber optic light supply, an optical aperture, an acoustic pressure transducer and an electric line for signal transmission to evaluation electronics. The sensor head and, in particular, the optical aperture are exposed directly to the liquid stream. The sensor is therefore highly susceptible to deposits on the optical aperture. Specifically, for use in a separating tank, it must be expected, because of the extreme and variable temperature and pressure conditions, that oillike and waxlike layers will result in pronounced coating formation.

U.S. Pat. No. 5,339,674 discloses a photoacoustic flow measuring cell for chemically aggressive gases. The optical aperture and the microphone are separated from the photoacoustic interaction zone by an elongate pipe and are additionally protected by an inert protective gas against being contaminated by the measurement gas. In this case, the pipe through which the gas flows serves as an optical transmission stage and, at the same time, as an acoustic waveguide. However, this measuring arrangement is unsuitable for liquid measuring cells because of the acoustic impedance jump between the liquid and the protective gas.

The prior art also specifies optical methods for the contactless detection of ultrasonic waves at surfaces. The article by Jean-Pierre Monchalin, "Optical Detection of Ultrasound", IEEE Transactions on Ultrasonics, Ferroelectrics and Frequency Control 33 (5), 485–499 (1986) describes optical sound detectors which are based on beam deflection or interferometric interference formation. Monolithically constructed interferometers suitable for everyday use, with integrated laser diode and photodiode, are nowadays obtainable commercially.

SUMMARY OF THE INVENTION

The object of the present invention is to specify an improved photoacoustic flow measuring cell for liquids, in which problems with the contamination of sensor components are largely avoided and which is distinguished by high measuring sensitivity and long term reliability. This object is achieved, according to the invention, by means of the features of claim 1.

The essence of the invention is, specifically, to produce an optically contactless photoacoustic liquid measuring cell by virtue of the fact that the measuring cell has a free fall stage for the liquid.

A first exemplary embodiment shows a flow measuring cell with a vertically falling cylindrical liquid jet and with a horizontal leaflike laser beam which excites, in the liquid column, plane acoustic waves which are detected by a piezoelectric acoustic pressure transducer externally on the outflow pipe.

A second exemplary embodiment constitutes a variant of the free fall measuring cell, in which a focused laser beam excites cylindrical acoustic waves in the liquid column and the resulting surface vibrations of the liquid column are measured completely contactlessly by means of an optical interferometer.

A third exemplary embodiment shows an installation of a photoacoustic free fall measuring cell, according to the invention, for measuring the concentration of oil in water in a high pressure separating tank.

Additional exemplary embodiments may be gathered from the dependent claims.

An important advantage of the photoacoustic cell according to the invention is that it is eminently suitable for measurements on chemically aggressive or coating-forming liquids.

Another advantage is that, despite the spatial separation between the analyte and the sensor components, good optical and acoustic coupling to the analyte is achieved.

Furthermore, the simple robust design without moveable parts, essential freedom from maintenance and the possibility of the in-situ remote monitoring of liquid analytes are advantageous.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Like parts are given the same reference symbols in the Figures.

DESCRIPTION OF THE PREFERRED EMBODIMENTS

Figure 1:
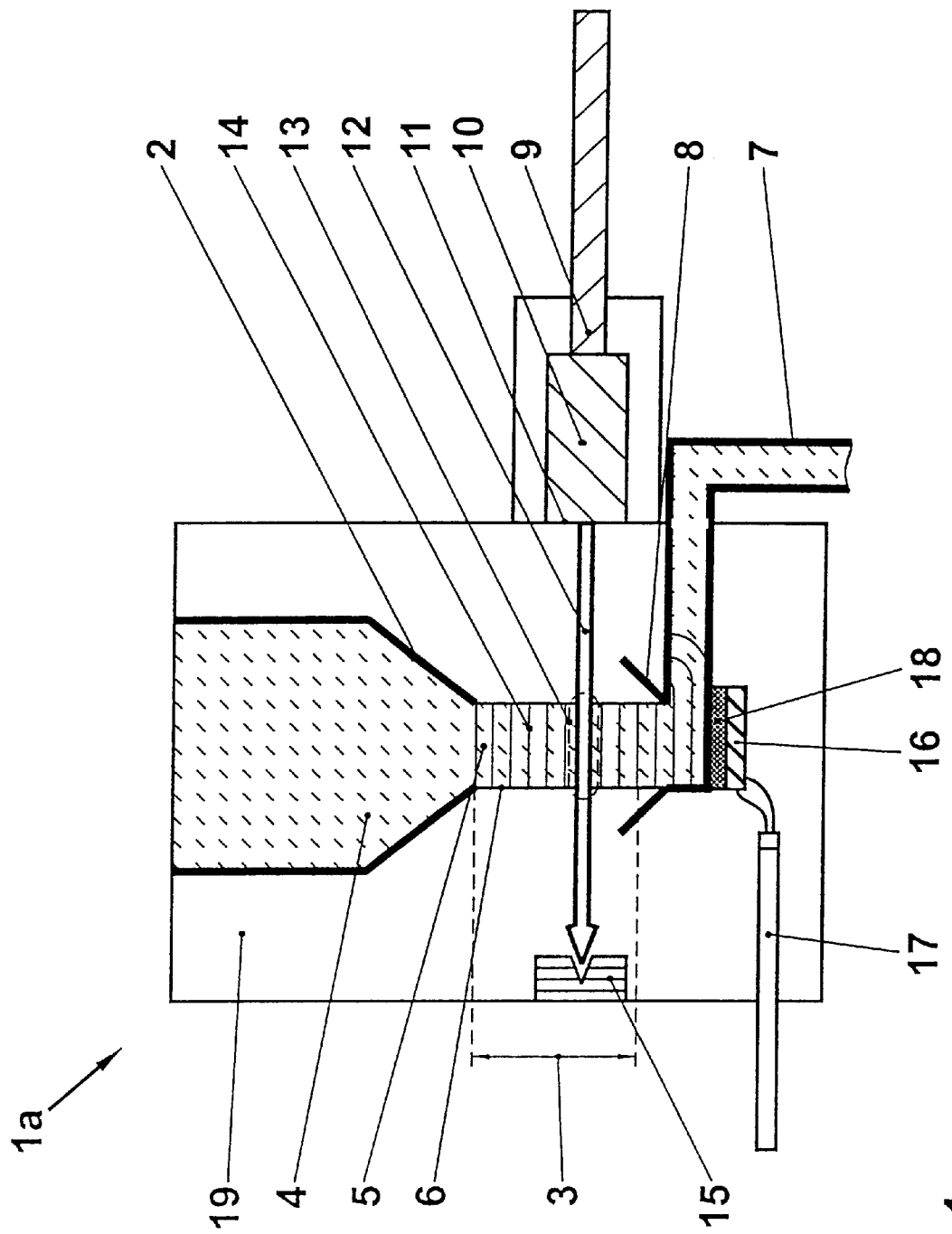
FIG. 1 shows a first photoacoustic free fall cell according to the invention, having a piezoelectric sound detector.

Referring now to the drawings, wherein like reference numerals designate identical or corresponding parts throughout the several views, the subject of the invention is a photoacoustic measuring cell $1a$, $1b$ for liquid analytes, in particular for measuring the concentration of oil in water. The photoacoustic measuring cell $1a$, $1b$ comprises means 2, 3, 7, 8 for deflecting the liquid flow 4, optical components for feeding in light or infeed optics 9, 10, 11, 21 and means 16, 17, 18, 23, 24 for sound detection.

FIG. 1 illustrates a first exemplary embodiment. The measuring cell $1a$ according to the invention has a free fall stage 3 for the liquid 4 to be investigated. It is essential to the invention that the liquid jet 5 is not guided in the region of the free fall stage 3, that is to say it is limited solely by its own surface 6. By contrast, there is a great degree of freedom with regard to the precise guidance of the liquid jet 5. In particular, a free fall stage 3 may also be designed for a horizontal or a curved jet 5. Preferably, the free fall stage 3 is designed for a cylindrical liquid jet 5 which, in particular, is oriented so as to fall vertically downward. For this purpose, the supply 2 for the liquid 4 is designed to be axially symmetric and conically tapering at the start or above the free fall stage 3. Mounted at the end or below the free fall stage 3 is an outflow pipe 7 which is preferably angled and is provided with a collecting funnel 8.

The measuring cell $1a$ comprises, furthermore, infeed optics 9, 10, 11, in particular a light source 9 or an optical supply fiber 9, which is connected to a light source, and focusing optics 10, for example a convex lens 10, which serves for the convergence of the sound-exciting light beam in the free fall cell $1a$. The free fall cell $1a$ may have an optical aperture 11 for protecting the convex lens 10. Advantageously, a protective gas 19 is provided between the free fall stage 3 and the infeed optics 9, 10, 11. The infeed optics 9, 10, 11 predetermine an optical axis or a light stage 12 in the measuring cell $1a$. A beam trap 15 for avoiding backscatter may be mounted at the end of the light stage 12. Preferably, the light stage 12 is oriented perpendicularly to the free fall stage 3. The light stage 12 intersects the free fall stage 3 and, in the overlap region, defines a photoacoustic interaction zone 13. In order to detect the acoustic waves 14 induced by light in the zone 13, the free fall cell $1a$ is equipped with a sound detector 16. In principle, there are no restrictions as regards the type and spatial arrangement of the sound detector 16. The sound detector 16 may, for example, be equipped with a piezoelectric or capacitive vibration transducer and be mounted below or above the free fall stage 3, in particular on the liquid supply 2 or on the outflow pipe 7. The free fall cell $1a$ is connected to measuring apparatus, not illustrated, via lines 9, 17.

Figure 2:
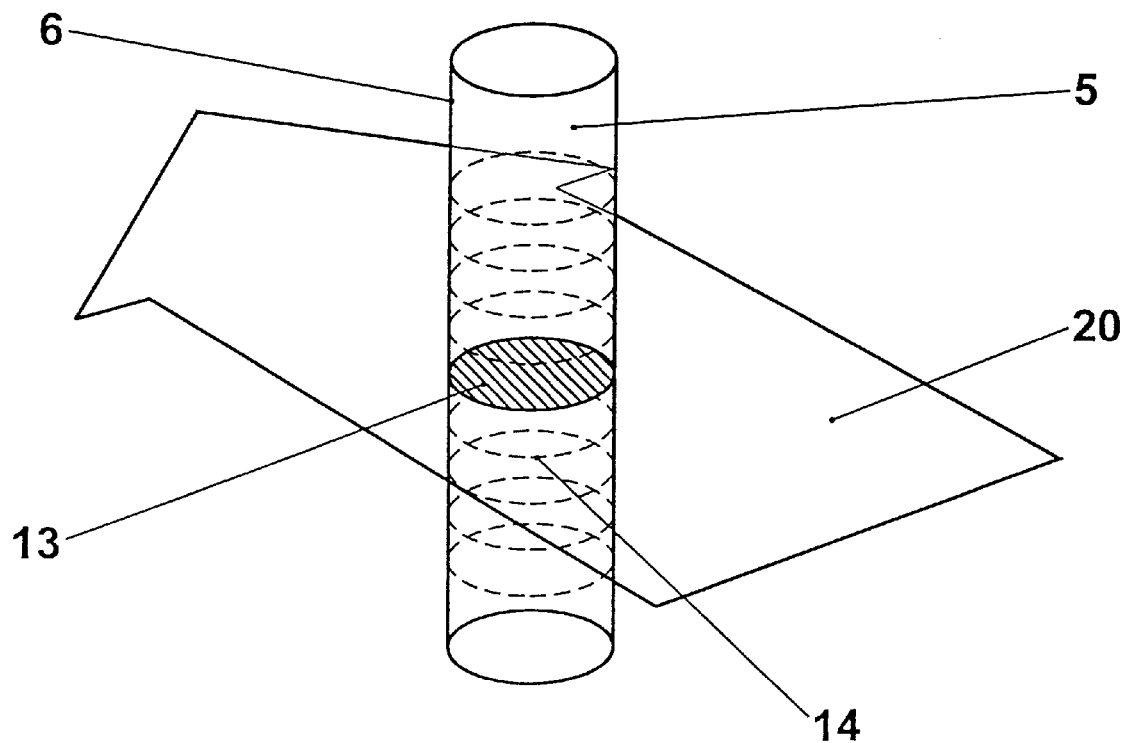
FIG. 2 shows a detailed view of the photoacoustic interaction zone in a free fall cell according to FIG. 1.

A preferred design according to the invention of the photoacoustic interaction zone 13 and of the sound detector 16 is explained in connection with FIG. 2. With the aid of cylindrical optics 10, in particular a cylindrical convex lens 10, a leaflike laser beam 20 is generated, which is propagated in a plane preferably perpendicular to the axis of the free fall stage 3 or of the liquid cylinder 5. In the illuminated cross section of the cylinder 5, plane acoustic waves 14 are generated photoacoustically, which are propagated on both sides along the cylinder axis or the free fall stage 3. A piezoelectric or capacitive sound detector 16 for detecting the wave running downward is fastened externally to the outflow pipe 7. For optimum acoustic coupling, the outflow pipe 7 is angled laterally at 90°, and the detector 16 is positioned in the angled region below the free fall stage 3. Furthermore, a layer 18 for acoustic impedance matching may be provided between the detector 16 and the outflow pipe 7.

A piezoelectric sound transducer 16 may consist of a piezoelectric ceramic, such as lead zirconates (PZT), or of an electrically polarized foil, such as polyvinyldifluoride (PVDF), Teflon or Mylar. The foil has the advantage of better impedance matching and a shorter reverberation behavior. Capacitive sound detectors 16, although being somewhat more complicated in technical terms, have a very high degree of detection of acoustic waves.

The arrangement according to the invention of the sound detector 16 is distinguished by high measuring sensitivity, along with low susceptibility to faults. Very good acoustic coupling is ensured, in that the light-induced ultrasonic waves pass through steel walls several millimeters thick and lime-containing or oil-containing inner wall coatings, without any appreciable attenuation, and are received highly efficiently due to the geometry of the outflow pipe 7. External mounting on the outflow pipe 7 is simple and reliable and protects the sound detector 16, together with the electric signal lines 17, against corrosion.

Another aim of the invention is to keep disturbing ultrasonic echoes, for example due to multiple reflections on the liquid surface 6, low. The planeness and vertical orientation, which are necessary for this purpose, of the acoustic waves 14 are achieved by means of a rectangular, wide beam profile homogeneous over the cylinder cross section and by a vertical beam-in direction of the laser leaf 29. For this purpose, cylindrical optics 10 with a horizontal beam spread greater than the orifice diameter of the supply 2 and with a markedly smaller vertical beam spread are selected. The resulting laser leaf 20 is then wider than the cylinder 5 and sharply delimited in the vertical direction.

In order to amplify the photoacoustic signal, resonant excitation of longitudinal vibrations of the cylinder 5 may be provided. For this purpose, the cylinder length L and the laser repetition rate f are coordinated with one another for a given sound velocity v. For example, for v=1500 m/s, L=1.5 cm and f=50 kHz, longitudinal cylinder vibration is excited.

Figure 3:
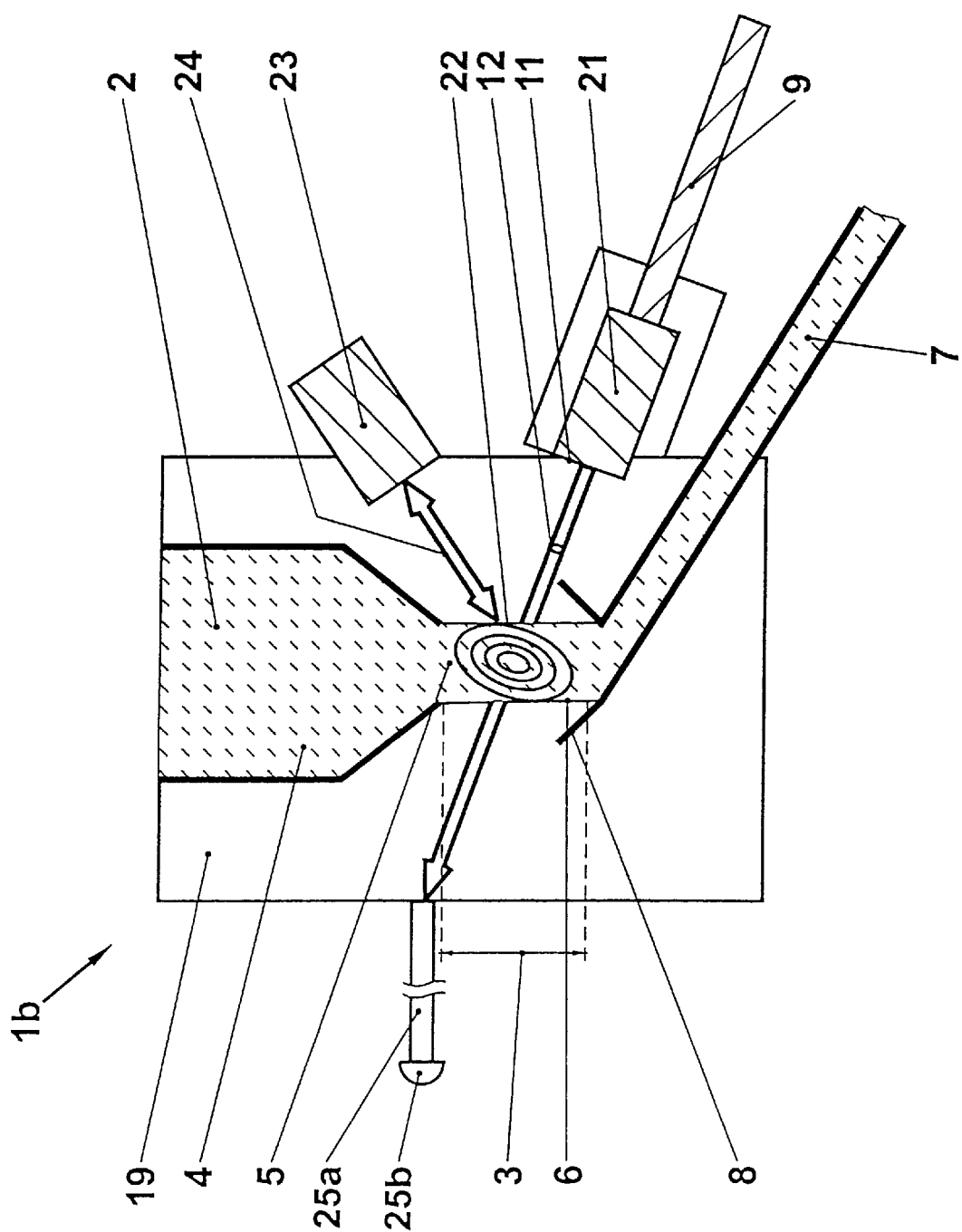
FIG. 3 shows a second photoacoustic free fall cell according to the invention, having an optical sound detector in the form of a monolithically constructed interferometer.

FIG. 3 shows a second embodiment of a free fall measuring cell $1b$ which is equipped, according to the invention, with an optical sound detector 23. The rest of the design of the measuring cell $1b$, in particular the arrangement of the free fall stage 3 and of the light stage 12, corresponds to the case presented above. In contrast to the measuring cell $1a$, here completely contactless sound detection is achieved. The measurement principle is based on the fact that the acoustic waves 22 induced photoacoustically by the light source 9 excite surface vibrations of the liquid jet 5, and these vibrations can be detected by means of an optical distance sensor or sound detector 23 of the type initially mentioned. The optical sound detector 23 is arranged so that there is visual communication with the free fall stage 3. A detection light beam 24 is oriented with respect to the free fall stage 3 in such a way that light reflected back or scattered back at the surface 6 can be recorded sufficiently by the detector 23.

Figure 4:
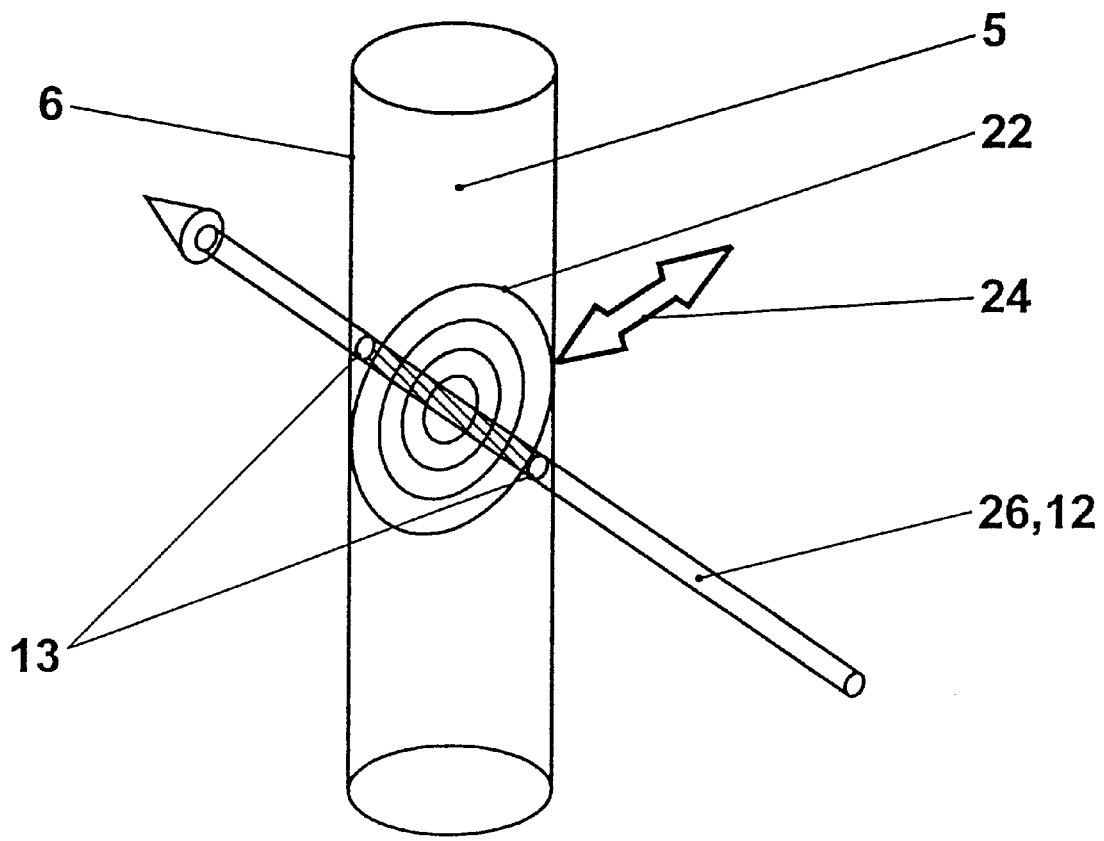
FIG. 4 shows a detailed view of the photoacoustic interaction zone in a free fall cell according to FIG. 3.

FIG. 4 illustrates a preferred design according to the invention of the photoacoustic interaction zone 13. With the aid of spheric infeed optics 21, in particular a spheric convex lens 21, a focused Gaussian or pencil-like laser beam 26 is generated which is propagated along the light stage 12. The light stage 12, in turn, is oriented preferably perpendicularly to the free fall stage 3 or perpendicularly to the axis of the liquid cylinder 5. In the illuminated part of the cylinder 5, cylindrical acoustic waves 22 are generated photoacoustically, which are propagated radially from the light stage 12 and set the surface 6 in vibration. High vibration amplitudes on the surface 6 will occur where the surface vector is directed perpendicularly to the light stage 12. The detection light beam 24 is therefore oriented preferably parallel to such a surface vector, that is to say perpendicularly to the light stage 12, and, of course, perpendicularly to the free fall stage 3.

Signal amplification may be achieved by the resonant acoustic excitation of transverse vibrations of the liquid jet 5. For thin liquid jets 5, higher excitation frequencies in the range of a few hundred kHz can be achieved in a simple way. Of course, here too, any desired cross sections of the liquid jet 5 can be selected by means of an appropriate shaping of the liquid supply 2 of the free fall stage 3. In particular, the supply 2 and, consequently, the liquid column 5 may have a rectangular or concave cross section. A concave surface 6 is suitable, for example, for achieving high acoustic resonances or for the optical convergence of the detection light beam 24 reflected back.

Preferably, the sound detector 23 is designed as a monolithic interferometer 23, in particular as a modulatable Michelson interferometer with an integrated laser diode and photodiode. The transmission exit and the reception entrance of the sound detector 23 are then located in the same place and the detection light beam 24 is oriented preferably perpendicularly to the surface 6, in order to maximize the intensity of the light reflected back into the detector 23. Optical fibers for coupling the optical sound detector or interferometer 23 to the measuring cell $1b$ may also be provided.

The liquid jet 5 is often subjected to concussions and other disturbing acoustic excitations which are to be eliminated in the interferometer signal. For this purpose, the Michelson interferometer 23 is regulated to a fixed operating point, so that low-frequency disturbances and drift in the sensor signal are compensated for. The high-frequency photoacoustic vibrations can then be measured, free of any disturbance, with a high degree of sensitivity.

Ultrasonic echoes caused by reflections at the liquid surface 6 are unavoidable in the free fall cell $1b$ according to FIGS. 3 and 4. The bandwidth of the optical detector 23 must advantageously be selected so as to be so great that the primary photoacoustic signal can be discriminated from the echoes. For example, for a diameter of the liquid jet 5 of 10 mm, the time interval of the echoes is 1 $\mu$s and the necessary bandwidth is a few MHz.

The considerations regarding the choice of the light source 9 and of the protective gas 19 are the same for both variants of the free fall cell $1a$, $1b$. The light source is preferably a semiconductor laser and, in particular, a laser diode. Laser diodes have high power and a long life, are insensitive to pressure, are commercially obtainable in the desired near infrared spectral range (for example, 0.7 $\mu$m–2.5 $\mu$m) and can be connected in a simple way via light guides. Preferably, pulsed laser diodes are used, the excitation frequencies of which are typically 100 kHz 10 MHz and lie outside the acoustic interference spectrum. Up to about 10 kHz, modulated continuous wave laser diodes may also be used. Fluctuations in the laser power can be monitored and corrected according to the invention by measuring the light power transmitted by the free fall cell $1a$, $1b$. For this purpose, the measuring cell $1a$, $1b$ is connected, at one end of the light stage 12, not to the beam trap 15, but, for example via an optical fiber $25a$, to an optical reference detector $25b$ which forms a signal proportional to the transmitted light power.

The measuring sensitivity and the measuring range may be varied by selecting the wavelength. In order to determine the concentration of oil in water with a high degree of detection, wavelengths near the absorption maxima of oils or oil constituents are selected. However, the dynamic range is then restricted by a saturation effect at higher concentrations. For measurements with a large dynamic range, wavelengths in spectral regions with only relatively weak oil absorption bands are selected. At all events, the background absorption in the water should be low. Advantageously, the wavelength of the laser diode 9 is selected in the spectral region between two water absorption bands, for example between 1.48 $\mu$m and 1.93 $\mu$m.

The protective gas 19 prevents the infeed optics 9, 10, 11 from being contaminated and damaged. For this purpose, said gas is chemically inert and is under a sufficiently high pressure. The protective gas 19 may be trapped, stationary, in the free fall cell $1a$ or circulate via delivery and discharge lines which are illustrated. Photoacoustic interactions in the protective gas 19 are harmless. Specifically, the impedance jump between the gas 19 and the liquid jet 5 is such that sound transmission from the gas 19 into the liquid jet 5 and from there to a sound detector 16, 23 is low. In particular, the natural gas occurring during the conveyance of oil may also be used as protective gas 19 instead of, for example, air, nitrogen or argon.

Figure 5:
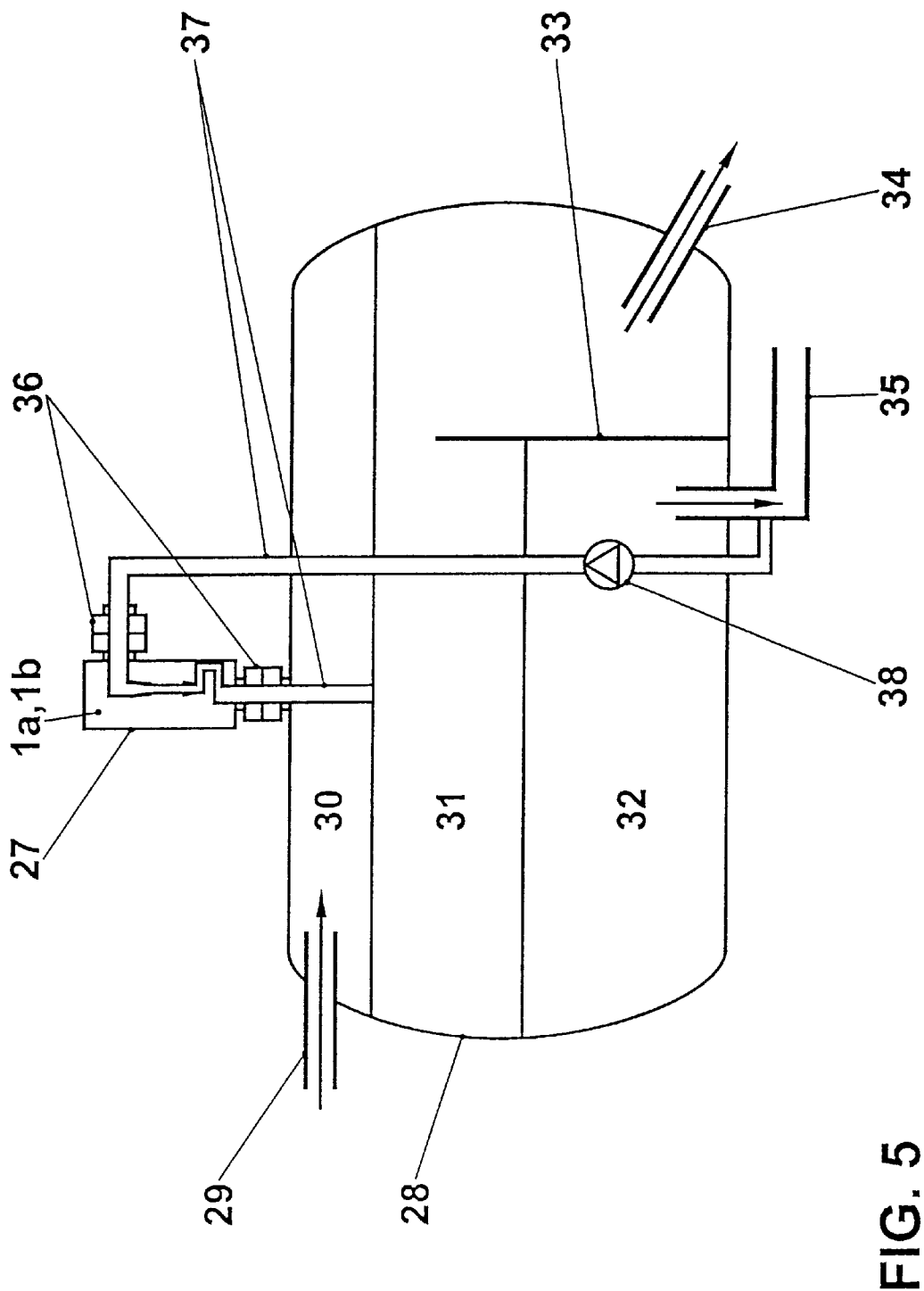
FIG. 5 shows an installation of a photoacoustic free fall cell in a high pressure separating tank.

In FIG. 5, a mounting according to the invention of the free fall cell $1a$, $1b$ on a high pressure separating tank 28 can be seen. The tank 28 is filled via an inlet 29. The phases, gas 30, oil 31 and water 32, are separated by sedimentation. The oil 31 is drained away through an outlet 34 and the water 32 through an outlet 35. The free fall cell $1a$, $1b$ is located in a pressure housing 27 which is connected to the water outlet 35 and the tank 28 via connections 36 and delivery lines 37.

The electric lines 17 and/or the fiber optic lines 9, 25a and the measuring apparatus are not illustrated. The flow 4 in the measuring cell 1a, 1b can be regulated by means of a pump 38. The internal pressure of the cell 1a, 1b corresponds to the pressure in the separating tank 28. The protective gas volume 19 in the free fall cell 1a, 1b may be exchanged with the gas 30 in the tank 28 by means of lines which are not explicitly illustrated.

The free fall cell 1a, 1b according to the invention has considerable advantages, as compared with the prior art. Contactless optical excitation makes it possible to avoid direct contact between the infeed optics 9, 10, 11 and the analyte 4, 5, 6. Devices for cleaning an optical aperture 11 and the aperture 11 itself may be dispensed with. The sound detectors 16, 23 are highly measurement-sensitive and are well protected from the analyte 4, 5, 6. A purely fiber-optically activated, electrically separated free fall cell 1b, without any active optic or electric components, can be produced by means of the optical sound detector 23. Such a free fall cell 1b is highly suitable for the in-situ remote monitoring of aggressive or contaminating analytes in environments with high temperatures, high pressures and pronounced electromagnetic disturbances.

Obviously, numerous modifications and variations of the present invention are possible in light of the above teachings. It is therefore to be understood that, within the scope of the appended claims, the invention may be practiced otherwise than specifically described herein.

What is claimed as new and desired to be secured by Letters Patent of the United States is:

1. A photoacoustic flow measuring cell for liquids, in particular suitable for measuring the concentration of oil in water, wherein:
   the measuring cell has a free fall stage for the liquid,
   a) the measuring cell is connected to an optical reference detector at one end of a light stage, and
   b) a pressure housing with connections for delivery lines is provided for mounting the measuring cell on a separating tank.

2. The photoacoustic flow measuring cell as claimed in claim 1, wherein:
   a) the free fall stage is designed for a cylindrical liquid jet falling vertically, and
   b) a protective gas is provided between the free fall stage and infeed optics.

3. The photoacoustic flow measuring cell as claimed in claim 2, wherein:
   a) the infeed optics comprise an optical supply fiber and a convex lens,
   b) the optical supply fiber is connected to a pulsed laser diode, and
   c) a light stage predetermined by the infeed optics is oriented perpendicularly to the free fall stage.

4. The photoacoustic flow measuring cell as claimed in claim 3, wherein:
   a) the convex lens is cylindrical,
   b) an angled outflow pipe is mounted at one end of the free fall stage, and
   c) a piezoelectric or capacitive sound detector is fastened externally to the outflow pipe.

5. The photoacoustic flow measuring cell as claimed in claim 3, wherein:
   a) the convex lens is spheric, and
   b) the measuring cell is equipped with an optical sound detector.

6. The photoacoustic flow measuring cell as claimed in claim 5, wherein:
   a) the optical sound detector is an interferometer, and
   b) a detection light beam of the interferometer is oriented perpendicularly to the light stage and perpendicularly to the free fall stage.

7. The photoacoustic flow measuring cell as claimed in claim 6, wherein optical fibers are provided for coupling the interferometer to the measuring cell.

* * * * *